(12) United States Patent
Eder (10) Patent No.: US 10,080,625 B2
(45) Date of Patent: Sep. 25, 2018

(54) GUIDE ELEMENT AND DEVICE FOR CREATING A HOLE IN A BONE

(71) Applicant: Jeder GMBH, Vienna (AT)

(72) Inventor: Klaus Eder, Perchtoldsdorf (AT)

(73) Assignee: Jeder GmbH, Vienna (AT)

( * ) Notice: Subject to any disclaimer, the term of this patent is extended or adjusted under 35 U.S.C. 154(b) by 0 days.

(21) Appl. No.: 15/391,367

(22) Filed: Dec. 27, 2016

(65) Prior Publication Data

US 2017/0105812 A1 Apr. 20, 2017

Related U.S. Application Data

(63) Continuation of application No. 13/884,188, filed as application No. PCT/AT2011/000406 on Sep. 30, 2011.

(30) Foreign Application Priority Data

Nov. 9, 2010 (AT) .............................. A 1839/2010

(51) Int. Cl.
| | |
|---|---|
| *A61C 1/08* | (2006.01) |
| *A61B 17/17* | (2006.01) |
| *A61C 8/00* | (2006.01) |
| *A61C 1/00* | (2006.01) |
| *A61C 3/03* | (2006.01) |

(52) U.S. Cl.
CPC ............ *A61C 1/082* (2013.01); *A61B 17/176* (2013.01); *A61C 1/0046* (2013.01); *A61C 3/03* (2013.01); *A61C 8/0092* (2013.01)

(58) Field of Classification Search
CPC ......... A61C 1/082; A61C 1/0046; A61C 3/03; A61C 8/0092; A61C 1/0061; A61B 17/176; A61B 17/1673
See application file for complete search history.

(56) References Cited

U.S. PATENT DOCUMENTS

| 4,021,921 A | 5/1977 | Detaille |
|---|---|---|
| 5,295,828 A | 3/1994 | Grosrey |
| 5,474,449 A | 12/1995 | Loge |
| 2008/0125856 A1 | 5/2008 | Perez-Cruet |
| 2008/0319466 A1 | 12/2008 | Eder |
| 2010/0167233 A1 | 7/2010 | Dricot |
| 2010/0178631 A1 | 7/2010 | Gordils Wallis et al. |

(Continued)

FOREIGN PATENT DOCUMENTS

| AT | 507 208 | 3/2010 |
|---|---|---|
| CN | 2516125 | 10/2002 |

(Continued)

*Primary Examiner* — Heidi M Eide
(74) *Attorney, Agent, or Firm* — Henry M. Feiereisen LLC (57) ABSTRACT

A guide element is constructed for arrangement on a device for the penetrating extension of a blind hole created in hard tissue, in particular in the jawbone, wherein the device includes a hollow body that forms a pressure chamber and that has a distal working opening and an inlet opening opposite the working opening. The guide element can be inserted into the inlet opening with a tight fit and the inlet opening can be closed by the guide element, the guide element has a through-hole, through which a shaft of a working tool, for example, of a milling tool, can be guided and inserted into the hollow body, and the guide element has a connection for a working medium for applying an internal pressure in the pressure chamber or in the hollow body

29 Claims, 4 Drawing Sheets

(56) References Cited

U.S. PATENT DOCUMENTS

2010/0324561 A1  12/2010  Watzek et al.
2011/0270236 A1  11/2011  Eder

FOREIGN PATENT DOCUMENTS

| CN | 201058047      | 5/2008  |
|----|----------------|---------|
| DE | 44 35 927      | 2/1996  |
| DE | 202006004954   | 7/2006  |
| EP | 1 269 933      | 1/2003  |
| JP | 2011-218054    | 11/2011 |
| RU | 1644922        | 4/1991  |
| SU | 1672924        | 8/1991  |
| WO | WO 2006/044073 | 4/2006  |
| WO | WO 2007/065978 | 7/2007  |
| WO | WO2007/129312  | 11/2007 |
| WO | WO2009/151926  | 12/2009 |
| WO | WO2010/048648  | 5/2010  |

GUIDE ELEMENT AND DEVICE FOR CREATING A HOLE IN A BONE

This application is a continuation of prior filed copending U.S. application Ser. No. 13/884,188, filed Jul. 18, 2013 which is the U.S. National Stage of International Application No. PCT/AT2011/000406, filed Sep. 30, 2011, which designated the United States and has been published as International Publication No. WO 2012/061854 and which claims the priority of Austrian Patent Application, Serial No. A 1839/2010, filed Nov. 9, 2010, pursuant to 35 U.S.C. 119(a)-(d).

BACKGROUND OF THE INVENTION

The invention relates to a guide element and a device for penetrating extension of a blind hole introduced into hard tissue, in particular into the jaw bone.

Such an extension of a bone bore is for example required in the filed of dental surgery when performing a procedure referred to as sinus lift. Sinus lift means an operation in which the mucosa of the maxillary sinus or sinus membrane or Schneider's membrane is partially detached and lifted to create a space between the bone and the mucosa of the maxillary sinus. Into the created hollow space, an autologous bone, for example from the tuber maxillae, the linea obliqua, the chin region or from the hip crest (bone replacement materials, bone graft) or a synthetic bone replacement material, for example bone replacement material of the brand Bio-Oss® from the company Geistlich AG, often mixed with autologous bone, is then introduced. This material is intended to convert into bone within 6 months, to ensure a solid base for an implant.

The conventional approach for a sinus lift is to prepare a mucoperiostal flap, buccally in the region of the molars, and to mill an oval window into the thus exposed bone, without damaging the underlying mucosa of the maxillary sinus. The oval bone disc which his attached to the mucosa of the maxillary sinus is then carefully pushed in the direction of the maxillary sinus, wherein the mucosa of the maxillary sinus is carefully detached from the bone around the window using special instruments. Because the mucosa of the maxillary sinus is very fragile, comparable to the chorion of an egg, this procedure has to be performed very carefully because of the risk of damaging the mucosa of the maxillary sinus. The space which is thus created in the maxillary sinus is then filled with the bone replacement material and the buccal window is covered with a film. Generally, the film is made of an absorbable material such as a membrane of the brand Bio-Gide® of the company Geistlich AG. After this, the mucoperiostal flap is densely sutured up. This method is relatively invasive and causes stress to the patient due to strong swelling and discoloration up to 10 days, and may also involve pain. This surgical procedure is often also referred to as "open" or "classical" sinus lift. In case a sufficient residual bone height remains, e.g. a height of 5 mm, the implants can be inserted at the same time of the sinus lift (one time sinus lift). The implants can be exposed to full load only after solidification of the bone replacement material. When the residual bone height is too thin, the insertion of the implants is performed in a second procedure about 6-8 months after the sinus lift (second sinus lift).

A newer method is the so called crestal sinus lift which does not require folding open of the bone plate. Access to the maxillary sinus is enabled from the jaw crest. At the toothless portion of the jaw crest, the oral mucosa is punched through up to the bone by means of a specially provided punch (Jesch's punch) and a blind hole is milled into the bone up to just below the mucosa of the maxillary sinus with a cylindrical milling machine. The punch used for this, automatically lifts the mucosal disc from the bone and creates a central through hole for the further bore or milling. The bore is milled below the bony sinus floor generally antral i.e., starting from the crest by means of a cylindrical milling tool for example with a diameter of 3.5 to about 1 mm, wherein the bone thickness is previously measured by means of X-ray. Because the mucosa of the maxillary sinus must not be damaged by the milling tool, the jaw bone must not be fully drilled through with the milling tool, so that at the bottom of the blind hole a thin bone plate remains, against the backside of which the mucosa of the maxillary sinus rests. Conventionally, this thin bone plate is then carefully pushed in the direction of the maxillary sinus with a cylindrical instrument, so that it is pushed in the direction of the maxillary sinus along with the mucosa of the maxillary sinus which is attached above the bone disc to the top of the bone disc. This "puncturing" of the bone disc is a critical point for the procedure because an excessive pushing-in of the bone disc leads to the mucosa of the maxillary sinus being lifted tent-shape and being tensioned, which may lead to damage to the mucosa of the maxillary sinus. The mucosa of the maxillary sinus is then carefully lifted, and the bone replacement material is then introduced into the newly created free space via the bore. The implant is then anchored mostly directly in the bore.

Even though very advanced methods have been developed to detach the mucosa of the maxillary sinus as carefully as possible and sufficiently far away from the jaw bone through the small bore, which mostly has a diameter of only about 4 mm, the moment at which the jaw bone is perforated remains a critical moment which requires great experience and particular skill of the doctor, wherein even when taking all precautions, there is still a residual risk of causing damage to the mucosa of the maxillary sinus when perforating the bone plate. In order to make the sinus lift-procedure safer, means are desired which facilitate this penetrating extension of the jaw bone bore, and at the same time lower the risk of damage to the fragile sinus membrane behind the jaw bone.

Such an advantageous means is known from WO 2010/048648 A1, where a device is described which has a tubular body with a distal working opening and an entry opposite the working opening, which entry is closed by a sealing element which is traversed by a shaft of a working tool, e.g. of a milling tool. On the tubular body, a connection for applying an internal pressure is arranged. The tubular body is sealingly inserted into a blind hole which was previously introduced into the jaw bone, wherein the distal working opening rests against the end of the blind hole thereby mostly sealing the inner space. The working medium inside the tubular body, preferably NaCl solution, can now be pressurized via the connection, for example by means of a syringe connected to the connection. With the working tool, which can be controlled from outside, the bone disc which remains between the blind hole and the maxillary sinus is milled off in the region of the working opening. At the moment when the head of the working tool penetrates the bone and enters into the region below the sinus membrane, the overpressure in the interior of the tubular body, causes the working medium to enter through the free opening and to push the sinus membrane located there behind away from the bone and with this out of the working area of the working tool and out of the zone of danger. The discharge of the working medium causes the pressure to decrease which indicates the perforation of the bone and also prevents an excessive bloating of the sinus membrane.

Such a device is safe to operate, and excellent surgical result with minimal risk to the mucosa of the maxillary sinus can be achieved with such a device. However, a certain disadvantage is that cleaning of the device is relatively costly and difficult. In particular, it is very difficult to clean the thin connection channel via which the pressure medium is supplied into the tubular body or the pressure chamber, thoroughly enough so that no contaminations remain. Generally, each reuse of medical equipment or products in the field of surgery bears certain infection risks for the patient and any contamination can lead to health problems, disease or even death of the patient. Although thorough re-sterilization of the device allows killing a predominant portion of the germs, such a re-sterilization is time consuming, exposes the material to stress and is cost intensive and still does not exclude a certain residual risk of a microbial contamination.

SUMMARY OF THE INVENTION

It is thus an object of the present invention to further refine the aforementioned device while still retaining its advantageous functionality, in that its contamination safety is increased and the risk of infection for the patient is lowered.

This object is solved by creating a guide element for arrangement on a device for perforating extension of a blind bore introduced into hard tissue, in particular into the jaw bone, which device includes a hollow body forming a pressure chamber with a distal working opening and an inlet opening opposite the working opening, wherein the guide element has a through hole for passage therethrough of a shaft of a working tool into the hollow body, wherein the guide element is constructed for form fitting engagement in the inlet opening of the hollow body of the device, to thereby close the inlet opening, and wherein the guide element has a connection for a working medium for establishing an inner pressure in the pressure chamber or in the hollow body.

This guide element according to the invention can be arranged as cost saving exchangeable component on the surgical device and can be used as expendable single use item.

The guide element is particularly suited, shaped and configured to be arranged on a device for penetrating extension of a blind hole introduced into hard tissue, in particular the jaw bone. Such a device includes a hollow body which forms an internal pressure chamber and has a distal working opening and an inlet opening opposite the working opening. This device essentially also corresponds to the device known from WO 2010/048648 A1.

The guide element according to the invention is insertable into the inlet opening of the device with a form fit, whereby the device can be sealingly closed by inserting the guide element. The guide element also has a through hole through which a shaft of a working tool, for example a milling tool can be passed and inserted into the hollow body of the device there underneath. In addition, a connection for supply of a working medium is provided in the guide element for establishing the required internal pressure in the chamber. This pressure serves for pushing away the sinus membrane after perforating the bone.

With this, the guide element according to the invention ensures that when applied correctly, a pressure chamber can be formed in the first place or a sufficient pressure can be built up. In addition, the pressure medium is also supplied exclusively via or through the guide element, in contrast to the device of WO 2010/048648, in which the pressure medium is supplied via a fixed, lateral connection socket which directly enters into the pressure chamber and is difficult to clean. Beside these two functions, the guide element also ensures that the shaft of the working tool is sealingly inserted into the blind hole and at the same time can be moved to remove the remaining floor plate.

A significant advantage is that the guide element can be exchanged, and after the intended use can be detached and discharged, which increases the safety of the surgical procedure and strongly decreases the risk of infection for the patient.

The guide element can thus be manufactured, distributed and stored as separate, aseptically packaged component similar to a syringe or syringe needle and is removed from the packaging just prior to the surgery and connected to the surgical instruments, and disposed after use. Such a disposal of the device of WO 2010/048648 would not be advisable, because this is an expensive precision component made of stainless steel. In this way, it is also ensured that a possible expiration date is observed or not exceeded and the operational safety is ensured.

Further advantageous embodiments of the guide element according to the invention are described in the dependent claims.

It is particularly advantageous when the guide element causes a pressure tight and essentially fluid tight closure of the inlet opening. Even though certain minor leakiness and/or leakage of pressure medium is tolerable, the required buildup of pressure and the maintenance of this pressure can be significantly better achieved when the guide element closes the inlet opening as tight as possible. A decrease in pressure which occurs when perforating the bone can also be detected better, faster and more reliably, and the milling tool can be stopped in time.

It is also very advantageous when the through hole of the guide element causes a pressure tight and essentially fluid tight support and guiding of the shaft, also in order to achieve the internal pressure in the pressure chamber of usually about 2 to 2.5 Bar in the first place and then maintain this pressure. At the same time, the through hole has to be configured so that at least one advance movement, drive and/or control movement of the shaft is ensured for example a rotation, a circular movement and/or an axial forward movement of the shaft when removing the floor plate of the blind hole, without significantly negatively affecting the sealing properties.

In this context, it is particularly advantageous when a sealing element, for example an O-sealing is arranged inside the through hole for further sealing the shaft. This ensures additional tightness of the system. In embodiments in which a conventional rotatingly driven milling tool is used, the sealing element functions as shaft sealing and has to seal the rotating shaft without excessively limiting its freedom of movement. This requires a relatively high quality of the sealing element and leads to a fast wear of the sealing element.

Configuring the sealing element one-piece or in one part, in particular as sterilisable, disposable plastic injection-molded part, has the advantage that it can be manufactured easily and cost effectively and ensures a contamination free working.

In a further advantageous constructive configuration of the guide element, the through hole is arranged in a disc-shaped head region of the guide element, preferably centered, and the connection is configured as socket for connecting a tube line and preferably extends radially outwardly.

In order to achieve a reliable supply of the working- or pressure medium, an inner channel which is closed from all sides can be formed in the guide element, which channel connects the connection with an outlet opening which leads into the inlet opening.

In this context, it is advantageously provided that the channel extends separate from the through hole over its entire extent.

It is particularly advantageous when a first subsection of the channel which is proximate to the connection, extends perpendicular to the central longitudinal axis of the through hole, and a second adjoining subsection of the channel is essentially parallel to the central longitudinal axis of the through hole. In this way, the channel can be worked into the guide element very easily for example also by subsequent borings.

In order to ensure a tight but nevertheless rotatable insertion of the guide element into the inlet opening, according to a further advantageous embodiment, a preferably cylindrical projection is formed on the side of the guide element which faces the inlet opening, and is preferably surrounded by a sealing element, for example an O-ring.

In a further advantageous embodiment, a tapered, frustrum-shaped sleeve which is open at its bottom is formed on the side of the guide element which faces toward the inlet opening, which sleeve is traversed centrally by the through hole. This extends the through hole and enhances the sealing effect, and the guiding of the shaft.

According to a particularly advantageous embodiment, the sleeve rests slightly closer and more sealingly against the shaft than the reaming portion of the through hole. The sleeve, in particular its front most distal section, thus contributes the most to the sealing and embraces the shaft particularly closely and tightly. The other sections of the through hole also seal well over their entire length but a certain play remains between the shaft and the inner surface of the through hole. This allows the shaft to slightly move radially, advantageously supported by flexible material properties of the guide element which allow for a certain distortion. Due to its small material thickness the sleeve is slightly more flexible anyway and permits tumbling movements of the shaft. With this, the sleeve improves the tightness as well as the movability of the milling tool.

Constructively, it is advantageous when the sleeve is formed on the cylindrical projection and the greater diameter of the sleeve is preferably smaller than the diameter of the projection.

Because according to an advantageous embodiment, the guide element is inserted into the surgical instrument with a rotating and pivoting movement, it is advantageous when the bottom side of the guide element which faces the inlet opening is smooth and planar, which enables an easy pivoting of the guide element.

It is advantages when a laterally projecting latching element is provided which can be reversibly latched into a corresponding latching through hole of the device, which ensures a safe operating position, but also easy removal.

In a further aspect, the invention relates to a device or a surgical instrument for penetrating extension of a blind hole introduced into hard tissue, in particular into the jaw bone. This device includes a working tool for example a milling tool, the guide element according to the invention and a hollow body which forms a pressure chamber. This hollow body has a preferably cylindrical inner hollow space with a distal working opening and an inlet opening opposite the working opening. The inlet opening is closed with the guide element, further, a shaft of the working tool is passed through or can be passed through the through hole and can be inserted into the hollow space of the hollow body. In addition, a tube line for introducing a fluid working medium for generating an internal pressure in the pressure chamber can be connected to the connection of the guide element.

With such a device, the above mentioned advantages are achieved and a safe and timely removal of the sinus membrane from the zone of danger i.e., the working area of the working tool is ensured. At the same time, the risk of contamination is significantly reduced, because the guide element can be exchanged.

According to a particularly advantageous embodiment, the drill head of the milling tool is significantly smaller than the blind hole and has a small-surfaced tip which may be strongly curved. This ensures a punctiform peroration of the bone plate which reduces the risk for the sinus membrane. In this way, the fluid can already flow through the small initial opening before the drill head breaks through with its entire diameter and would come into contact with the sinus membrane. A large-surface initial perforation of the bone plate, as would be the case with flat drill heads, is not advantageous.

Advantageous embodiments of this device provide for example that the guide element closes the inlet opening, and with this the pressure chamber, pressure tight and essentially fluid tight and a preferably constant pressure of at least 2 bar can be achieved inside the pressure chamber.

It is further advantageous that the shaft is supported and guided in the through hole in a pressure tight and essentially fluid tight manner and a preferably constant pressure of at least 2 bar can be reached inside the pressure chamber, however, at the same time at least an advance movement, drive movement, and/or control movement of the shaft for example a rotation, a circulating motion and/or an axial advance movement of the shaft is ensured. As mentioned before, this allows reaching and maintaining the pressure required for pushing away the sinus membrane, at simultaneous retention of the movability of the working tool.

In order to ensure an easy removability of the guide element and to prevent that the guide element is reused as a result of negligence, it is advantageous when the guide element can be attached reversibly and destruction free on the hollow body and is easily and simply removable from the same.

A very easy handling can be achieved in that a handle element is arranged on the hollow body. With this, the surgeon or dentist can securely place the hollow body in the blind hole and remove the hollow body again.

A constructively advantageous and easy to use embodiment is achieved in that the guide element is arranged in a recessed region on the distal end of the handle element.

When the tube line extends in a, as the case may be with fixing elements provided in the handle element formed groove, it is ensured that the tube line is supported securely and space effectively and a bending or unintended tearing off from the connection is not possible.

In order to achieve a stable operating position, according to an advantageous refinement, a latching through hole can be formed preferably in the border surface of the recessed region, into which latching through hole the corresponding latching element of the guide element can be clicked and the guide element can be fixed in this position, wherein the engagement occurs in particular by a rotating and pivoting of the guide element by about 30° to 50° with the through hole as rotation axis.

In this context, it is advantageous in particular in order to achieve an easy rotatability, when the guide element is insertable into the inlet opening with the cylindrical projection in a fluid tight manner, in particular up to a stop.

In order to make it possible to supply the pressure medium and simultaneously pass the shaft through the through hole through the guide element, it is advantageous when the outer walling of the sleeve is spaced apart from the funnel-shaped inner walling of the inlet opening.

For sealing insertion into the jaw bore, the uppermost portion of the hollow body which is to be inserted into the blind hole, can be configured conical. The conical region can be pressed into the blind hole by applying manual force. This is advantageous in particular when a handle extension is provided which impedes a rotation of the instrument which has been inserted into the bore in the mouth region. The rotation of the instrument can serve for screwing the instrument into the bore. For this purpose, in a further embodiment, a self cutting thread can be provided on the hollow body in the region which is to be introduced into the blind hole. This ensures a secure fit of the hollow body in the bore and improves the sealing against to the inner walling of the bore.

In order to further improve the sealing, a flange which can be provided on the outside of the hollow body and can be adjusted along the hollow body and detachably fixed to the hollow body, has a conical sealing attachment which reaches between the hollow body and the walling of the blind hole. This flange is pressed against the oral mucosa with the cone and then fixed for example by means of an Allen screw, thereby also closing this end of the pressure chamber pressure tight.

In order to achieve a slow forward feed of the milling head and to avoid an abrupt advance as far as possible, an elastic bellow can be arranged between the guide element and the working tool.

According to a further advantageous embodiment, the working tool is a rotatingly driven working tool for example a milling tool, or a rotation-free working tool, for example an ultrasound osteotome or a laser cutting device. Such working tools are described in detail in WO 2010/048648 A1 and are hereby incorporated by reference into the present application. In the context of this invention, rotation-free means that the working tool and the sealing element contact one another essentially without the occurrence of relative velocities, because the working tool does not rotate about its main axis. As a result, a rotating shaft does not have to be sealed by means of a rotation shaft sealing, which lowers the stress on the sealing element.

The working tool can be a piezoelectric surgical instrument, preferably an ultrasound ostetome which operates in a range between 20 and 200 micrometers. As an alternative, the working tool can be a laser cutting tool which has preferably a pulsed CO2-Laser or a solid-state laser, wherein the wavelength of the laser is preferably adjusted to the absorption characteristics of the bone tissue and can be coupled with an endoscope.

In a further advantageous embodiment of the invention, the milling tool can be connected with a manual or automatic control unit via the connection. This enables an exact regulation and control of the internal pressure, wherein the perforation of the bone can be immediately recognized by way of the decrease in pressure and the milling tool can be switched off if necessary.

When the apparatus has a device for generating or transmitting mechanical or electromagnetic vibrations, additional vibrations, preferably pressure-free ultrasound vibrations can be introduced into the system or the working medium in order to accelerate detachment of the sinus membrane.

In a further advantageous embodiment, the diameter of the shaft decreases toward the drill head with at least one step. The partial section of the shaft which lies in the region of the pressure chamber has a smaller diameter than the partial section of the shaft which lies sealingly in the region of the through hole. In this way, the shaft is sealingly supported in the through hole, however, a pressure chamber of sufficient size remains and the shaft has sufficient mobility to allow removal of the remaining bone plate as completely as possible.

The invention also relates to a set including the guide element according to the invention and a tube line for connection to the guide element and optionally a syringe for generating the required internal pressure, wherein the guide element and the tube line as well as the syringe are sterilized and aseptically packaged in a closed container, preferably a plastic bag. This facilitates storage and handling and ensures contamination free working.

Further advantages and embodiments of the invention become apparent from the description and the included drawings.

BRIEF DESCRIPTION OF THE DRAWING

The invention is now schematically shown by way of a particularly advantageous exemplary embodiment in the drawings, which is not to be understood as limiting, and is exemplary described with reference to the drawings:

FIG. 4 shows the insertion of the guide element into the hollow body.

FIG. 5 shows the pivoting of the inserted guide element.

FIG. 6 shows the device after the latching engagement with of the guide element.

FIG. 7 shows a cross section through the device with inserted shaft of the working tool at the time point of perforation of the working tool through the bone plate.

DETAILED DESCRIPTION OF PREFERRED EMBODIMENTS

Figure 1:
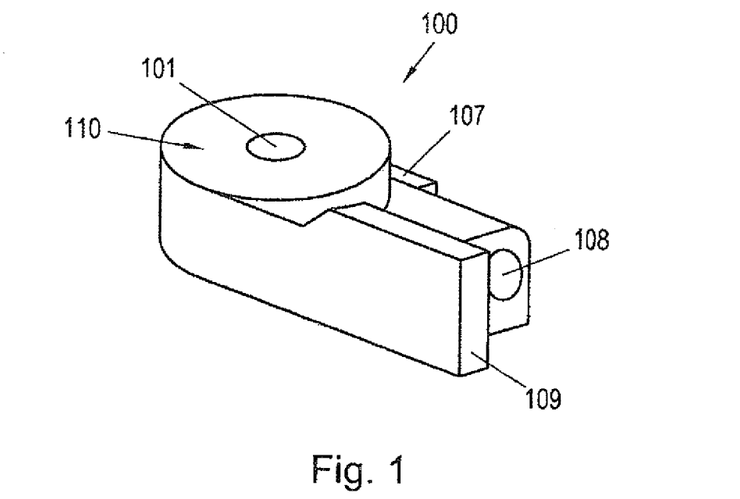
FIG. 1 shows the guide element according to the invention in a perspective view obliquely from above.

FIG. 1 shows a particularly preferred exemplary embodiment of the guide element 100 according to the invention in an oblique view from above. The here shown guide element 100 is formed by a sterilizable polymer, as it is known in the field of medical technology. The guide element is configured one-piece or as one part and is produced by means of injection molding. However, sealings and bores can be performed subsequently.

In a disc-shaped head region 110 of the guide element 100, a cylindrical through hole 101 is formed centrally, which completely traverses the guide element 100. During operation, the shaft 5 of a working tool 6, for example a milling tool is passed through this through hole 101. The diameter of the through hole 101 is slightly greater than the diameter of the shaft 5 of the working tool 6, so that the milling tool 5, 6 remains movable in the hollow body 1, and working medium can flow around the milling tool 5, 6.

Adjoining this head region 110 is a connection 108 in the form of a socket for fastening a tube line 111 which is not shown in this Figure. The tube line 111 is inserted into this socket. The connection 108 extends radially and outwardly from the center of the through hole 101, and the central longitudinal axis lies in the plane of the disc-shaped head region 110 which plane is oriented parallel to the surface.

Adjacent to the connection 108, a projecting nose 109 is formed, which extends tangentially from the head region 110 parallel to the connection 108 and protrudes height wise as well as longitudinally over the connection 108. The nose 109 serves on one hand for securing the connection of the tube line 111 and for better grip during pivoting.

Between the head region 110 and the connection 108, a slightly downwardly offset, projecting latching element 107 is molded with which the guide element 100 can be reversibly fastened to the device.

As can be seen in FIGS. 3 to 7, a cylindrical elevation which is arranged around the through hole 101 can be formed on the topside of the guide element 100, in particular for improving the guiding and the tightness.

Figure 2:
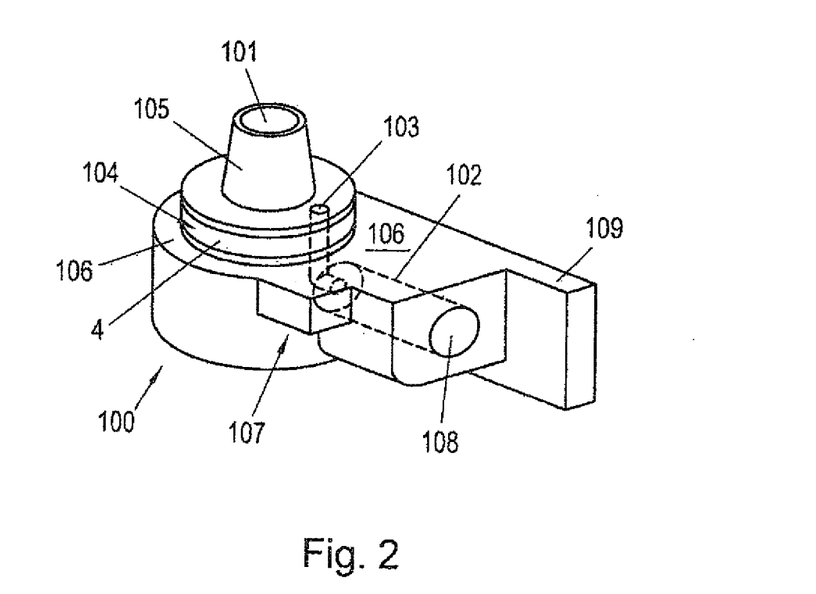
FIG. 2 shows the guide element according to FIG. 1 in a view oblique from below.

FIG. 2 shows the guide element 100 from the opposite side obliquely from below. The bottom surface 106 of the guide element 100, which bottom surface 106 faces the bone 24 during operation, is smooth and planar, which ensures a good slidability and rotatability and pivotability. A cylindrical projection 104 is formed in the head region 110, and is surrounded by a sealing element 4 in the form of an O-ring which is retracted in a groove. With this, the guide element 100 is form fittingly inserted into the device, as described in the following Figures.

An upwardly tapered frustrum-shaped sleeve 105, is molded on the projection 104. The greatest diameter on the base of the sleeve 105 is about 30 to 40% smaller than the diameter of the cylindrical projection 104.

Like the head region 110, the cylindrical projection 104 and the sleeve 105 are arranged concentrically around the central longitudinal axis of the through hole 101 and are traversed in their center by the through hole 101.

A channel 102, which is closed from all sides and is located completely inside the guide element 101, extends from the connection 108 and connects the connection with the outlet opening 103. The outlet opening 103 leads out at the bottom surface of the cylindrical projection 104 adjacent the sleeve 105 and ensures introduction of the fluid working- or pressure medium, in most cases physiological saline solution, into the inlet opening 3 of the device. The channel 102 is separated from the through hole 101 along its entire extent. The channel 102 has a first subsection which is near the connection 108 and has an initial greater diameter, and is oriented perpendicular and radially relative to the longitudinal axis of the through hole 101. The diameter of the channel 102 then decreases and the channel turns at a right angle. This adjoining second subsection extends essentially parallel to the central longitudinal axis of the through hole 101. In this way, the channel 102 can be formed constructively simple in the one-piece guide element, for example by two subsequent bores.

Figure 3:
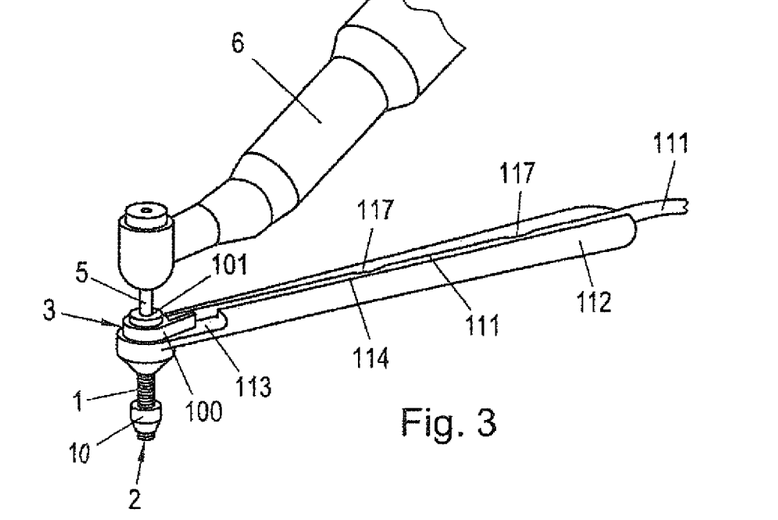
FIG. 3 shows the entire device with the guide element according to the invention, the hollow body and a working tool.

FIG. 3 shows the device according to the invention in a perspective view. This exemplary and not limiting device for penetrating extension of a blind hole in the jaw bone 24 includes a working tool 6 in the form of a milling tool 6, and the guide element 100 described above which is fixedly connected with a hollow body 1.

The hollow body 1 is arranged on a handle element 112 which has the shape of a flat small rod. The guide element 100 is arranged in a recessed region 113 on the front end of the handle element 112. The hollow body 1 has an essentially cylindrical inner space 12, a distal working opening 2, and an inlet opening 3 opposite the working opening 2. Through this inlet opening 3 the pressure medium as well as the shaft 5 of the working tool 6 is inserted into the hollow space 12 of the hollow body 1. The hollow body 1 is essentially constructed as the tubular body described in WO 2010/048648.

In order to be able to form a pressure chamber 7 inside the hollow body 1, it is necessary to seal the hollow space 12 of the hollow body 1 and the shaft 5 of the milling tool 6 in the region of the inlet opening 3. This pressure chamber 7 and the pressure generated therein, ensure that the sinus membrane 26 is timely pushed away of out of the zone of danger when perforating the bone plate.

The formed pressure chamber 7 can either be located completely inside the hollow body 1, when the working opening 2 is sealingly flush with the bottom of the blind hole. However, the pressure chamber 7 can also extend up to a region outside the actual hollow body 1, which is delimited by the walling of the blind hole and the conical sealing unit or the flange 10. During operation, both these features have a sealing effect and complement each other in order to maintain the system as pressure tight and fluid tight as possible.

The inlet opening 3 on the other end of the pressure chamber 7 is closed in a pressure tight and fluid tight manner by the tightly and form fittingly inserted guide element 100. In addition, the shaft 5 is already inserted and traverses the through hole 101, however, it does not yet exit through the working opening 2, and is thus not yet operational. In the connection 108, the tube line 111 is already connected, thus enabling supply of pressure medium into the inside of the hollow body 1. The tube line 111 extends in a recessed groove 114 which is configured as handle element 112. This groove is bent meander-shaped at two points in order to fasten the tube on these fixing elements 117. The tube line 111 can lead to a syringe or to a manual or automatic pressure control unit, with which the pressure can be introduced and controlled.

Figure 4:
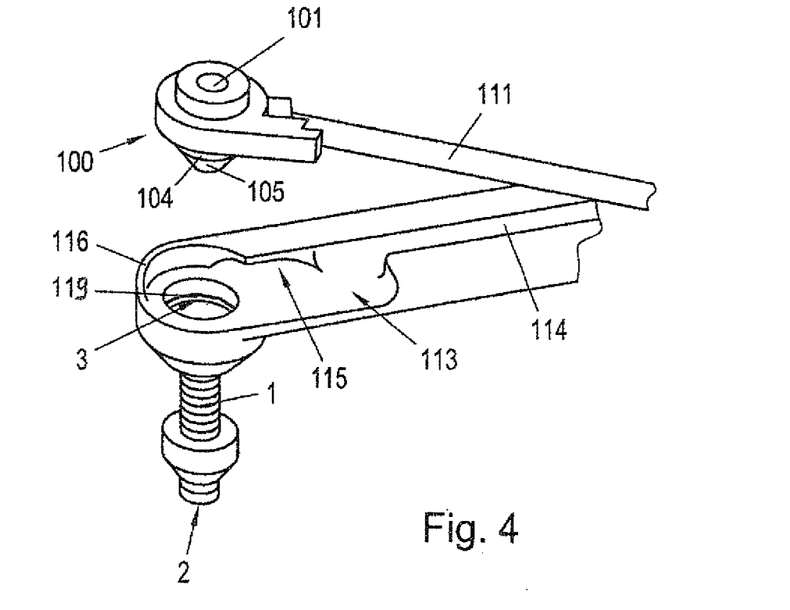
FIG. 4 to 7 show stepwise the preparation and assembly of the device.

FIGS. 4 to 7 show the stepwise preparation of the device for the procedure:

In FIG. 4, the guide element 100 is already connected with the tube line 111 however, not yet attached to the hollow body 1. In the front portion of the handle element 112, the recessed region 113 can be recognized in which the guide element 100 is arranged. In the front-most distal region of the recessed region 113, the inlet opening 3 is arranged, which defines the access to the inner hollow space 12 of the hollow body 1. The inlet opening 3 is initially very wide and configured cylindrical in a first section up to a stop or a circumferential stop surface 119 which has a decreased diameter relative to the through hole 101. In this cylindrical region, of the inlet opening 3 the cylindrical projection 104 of the guide element 100 is inserted form fittingly, wherein the bottom surface of the cylindrical projection 104 then rests on the stop 119. This ensures a secure rotatability or pivotability and simultaneous guiding and tightness, wherein the central longitudinal through hole 101 forms the rotation axis.

The inlet opening 3 is tapered downwardly conically and forms a funnel shaped hollow region. Inside the hollow body 1 extends the essentially cylindrical hollow space 12 up to the working opening 2.

Figure 5:
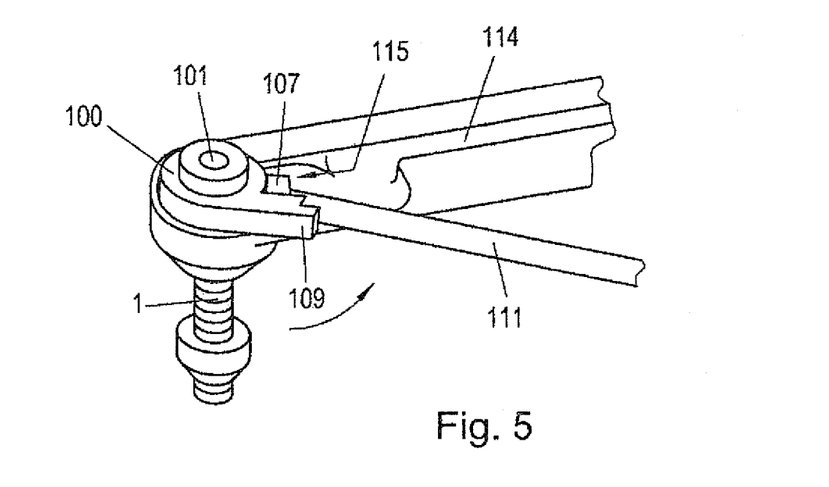

In FIG. 5, the guide element 100 is already form fittingly and sealingly inserted into the inlet opening 2 with the projection 104. The guide element 100 is then rotated or pivoted by about 30° to 40° in the direction of the arrow, until the connection 108 essentially points toward the start of the groove 114. Practically, the pivoting is carried out by gripping and applying pressure on the nose 109. The latching element 107 can be latchingly engaged in a form fitting and force fitting manner into the corresponding latching recess 115 in the handle element 112, more specifically into the vertical border surface of the recessed region 113, thereby fixing the guide element 100 in position.

Figure 6:
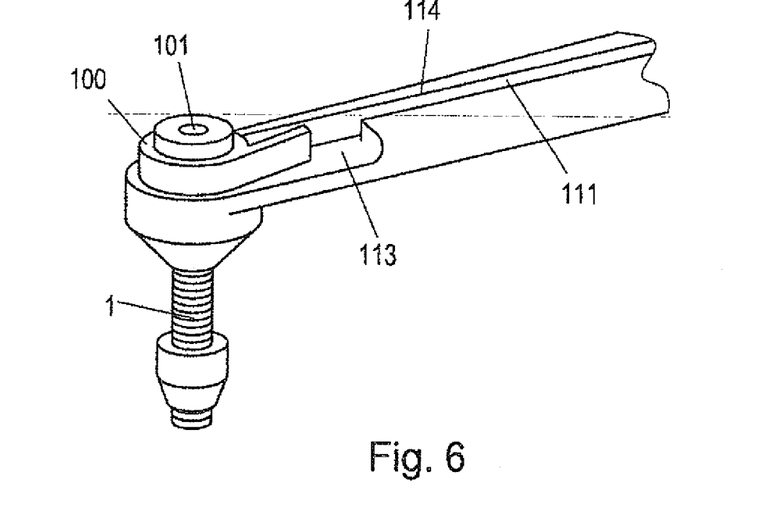

In FIG. 6, this engagement has already occurred and the tube line 111 is also already inserted and fixed in the rove 114. The device is now prepared and in practice the hollow body 1 is now sealingly inserted into the pre-drilled blind hole in the jaw bone 24 of the patient.

Figure 7:
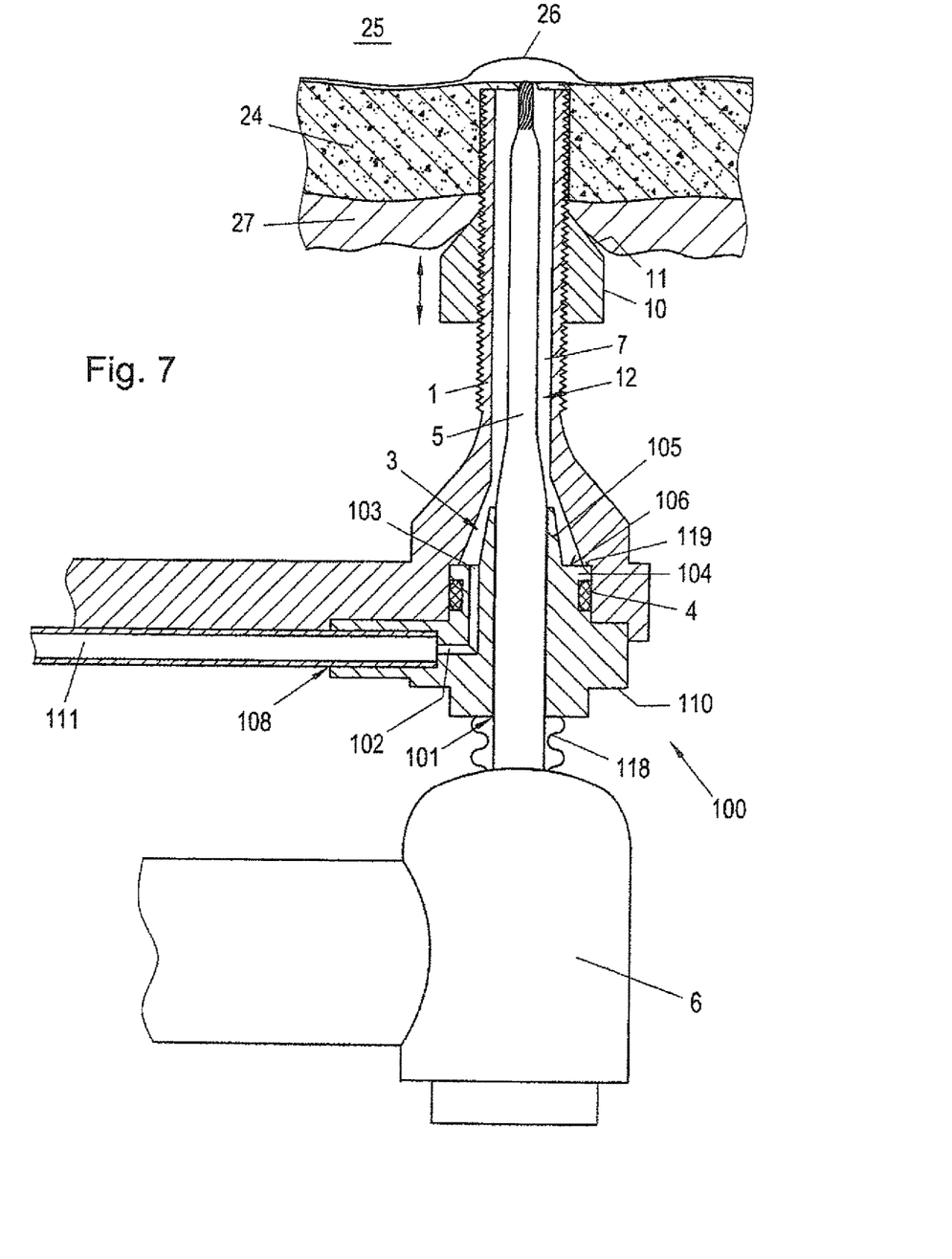

FIG. 7 shows a cross section through the device with inserted shaft 5 of the working tool 6 during a sinus lift at the time point when the working tool 6 perforates the bone plate of the haw bone 24 of the upper jaw. FIG. 7 shows the device in its spatially correct positioning in practice relative to the patient.

As in the conventional crestal sinus lift, a blind hole is introduced into the jaw bone 24 in a prior procedure starting from the jaw crest, wherein an approximately 1 mm deep bone plate remains between the end of the blind hole and the maxillary sinus 25. This is necessary in order to prevent damage to the mucosa of the maxillary sinus 26 which rests against the jaw bone 24 in the maxillary sinus 25.

Then, the hollow body 1 is sealingly inserted into the prepared blind hole, until the working opening 2 abuts the bone plate. The hollow body 1 stands still during the procedure, is fixed in position and can even be screwed in.

For improving the sealing effect, the flange 10 is shifted on the tube body 1 towards the jaw bone 24, so that the conical sealing portion 11 which is arranged on the flange 10 is strongly pushed against the oral mucosa 27 at the outer border of the blind hole, and the blind hole is sealed. Optionally, a cofferdam can also be used. Inside the pressure chamber 7, a hydrostatic pressure of about 0.5 to 3 bar can then be established.

The working medium in the pressure chamber 7 serves simultaneously for dissipating heat generated by the milling and as lubricant for the rotating shaft 5. Small amounts of working medium which can leak along the rotating shaft 5 do not pose a problem for the functionality of the device, because the pressure of the working medium can be maintained in the pressure chamber 7 via the connection 108. Good sealing properties are nevertheless very advantageous because the pressure decrease at the moment of perforation of the bone plate can be more readily recognized when the pressure chamber is sealed tight.

After this, the shaft 5 of the working tool 6 is inserted through the through hole 101 and the inlet opening 3 into the inside of the hollow body 1. The diameter of the shaft 5 is configured to decrease toward the tip. Thus, the diameter of the shaft 5 decreases in the region of the entry point of the inlet opening 3 by about one quarter. As a result, sufficient space remains between the shaft 5 and the inner surface of the hollow space 12 to form the pressure chamber 7 and to provide sufficient freedom of movement for the milling tool to perform tumbling movements. In the end side region of the drill head of the milling tool 6, the diameter decreases again by one quarter. In addition, the outermost tip or the drill head of the milling tool 6 or the shaft 5 is relatively strongly curved or essentially configured punctiform in order to ensure as much as possible a punctiform, small-surface perforation through the bone plate.

The shaft 5 traverses the through hole 101, the inlet opening 3 and the inner hollow space 21 of the hollow body 1 completely and exits through the working opening 2, so that the remaining bone plate can be worked on. The distal region of the shaft 5 with smaller diameter can be guided through the through hole 101 relatively easily, the rear region with greater diameter then comes to sit form fittingly in the through hole 101.

The shaft 5 thus sealingly rests against the inner surface of the through hole 101 in this region or is additionally also sealed, guided and supported in the region of the cylindrical projection 104 and the sleeve 105. Inside the through hole 101, an additional sealing for example an O-ring can also be provided however, this is not the case in the present exemplary embodiment. An elastic bellow 118 can be arranged between the guide element 100 and the working tool 6.

Nevertheless, the shaft 5 is movable axially, i.e., upwards and downwards according to the arrow, which is required especially in the case of rotating milling tools 6 in order to achieve the necessary forward advance for milling through the bone plate in the jaw bone 24. In addition, it is further possible, for example due to the flexibility of the material of the guide element 100, to move the shaft 5 in a rotating or tumbling movement, to remove the bony floor plate as expansively and completely as possible.

This rotating movement is also possible when using a working tool with a shaft 5 which rotates about its own axis. The shaft 5 is nevertheless supported fluid tight and pressure tight especially in the region of the sleeve 105, and a sufficient pressure can be built up in the pressure chamber 7 when the hollow body 1 is sealingly inserted into the blind hole.

Via the connection 108, the working medium, for example a physiological saline solution, can now be introduced into the inlet opening 3. Because the outer walling of the sleeve 105 is spaced apart from the inner walling of the funnel-shaped inlet opening 3, the rinsing medium flows outside along the sleeve 105 and along the shaft 5 into the inner space 12 or the pressure chamber 7.

The milling tool 6 in FIG. 7 is then progressively moved further downward, so that the milling head exits at the lower end through the working opening 2 and touches the floor plate, wherein the advance of the shaft 5 or the milling tool 6 is very slow, for example about 1 mm/min.

As soon as the floor plate is perforated minimally at one point, which is facilitated by the punctiform drill- or milling head, the pressurized working medium immediately exits through this minimal opening and the sinus membrane 26 is immediately pushed out of the zone of danger away from the drill head and slightly detached from the jaw bone 24, before the drill head can fully traverse the opening. This corresponds to the situation shown in FIG. 7.

The milling tool is then turned off and the sinus membrane 26 is further detached as known from WO 2010/048648 in order to increase the space for the bone replacement material, for example by additional supply of pressure medium and as the case may be, by introducing vibrations.

The shaft 5 can remain in the through hole 101 as sealing element for the time being. As an alternative, the shaft 5 can also be removed and the through hole 101 can be sealingly closed by inserting a stopper. This allows to further exert pressure or to maintain the pressure constant.

As the case may be, vibrations, for example ultrasound vibrations, can be introduced into the medium to facilitate a further detachment of the sinus membrane 26.

For exchanging or removing the guide element 100 after the procedure, the guide element 100 is gripped at the nose 109 and pivotally rotated in the opposite direction indicated by the arrow in FIG. 5. In the front most region of the handle element 112, a continuously increasing outer border 116 is formed, which interacts with the bottom surface 106, forces the guide element 100 upwards during the pivoting and eventually lifts the guide element 100 out of the inlet opening 3.

According to the invention, it is further provided that the guide element 100 is distributed as sterilized and aseptically packaged disposable item or medical product either by itself or combined with the tube line 111. Just prior to starting the procedure, the surgeon or dentist can tear open the packaging and remove the guaranteed contamination-free guide element 100 and the tube unit 111, fasten the same to the hollow body 1 and arrange the working tool correspondingly.

For the functionality of the device and in particular the application on the patient reference is made to the discussion in WO 2010/048648 A1.

The invention claimed is:

1. A device for penetrating extension of a blind bore introduced into hard tissue, in particular into the jaw bone, comprising: a working tool having a shaft;
   a hollow body forming a pressure chamber, said hollow body being constructed for sealing insertion into the blind bore and having a working opening, and an inlet opening opposite the working opening;
   a tube line; and
   a guide element configured for placement into the inlet opening and having a through hole constructed for guiding therethrough the shaft of the working tool into the hollow body, said guide element having a connection for connection to the tube line, wherein a channel extends in the guide element separate from the through hole from a first opening formed on the connection to a second opening formed axially offset relative to the through hole on an axial end side of the guide element and leading into the hollow body.

2. The device of claim 1, wherein the working tool is constructed as a milling tool.

3. The device of claim 2, wherein the milling tool has a drill head, said drill head having a pointed end and a curved configuration.

4. The device of claim 1, wherein the pressure chamber is configured cylindrical.

5. The device of claim 1, wherein the guide element is form fitted in the inlet opening, with the shaft of the working tool being received in the through hole of the guide element, such as to maintain inside the pressure chamber a pressure of at least 1.5 bar.

6. The device of claim 5, wherein the shaft is supported and guided for movement in the through hole in a pressure tight and essentially fluid tight manner.

7. The device of claim 6, wherein the movement includes a member selected from the group consisting of a rotating movement, a circulating movement, a tumbling movement and an axial movement.

8. The device of claim 1, wherein the guide element is form fitted in the inlet opening, with the shaft of the working tool being received in the through hole of the guide element, such as to maintain inside the pressure chamber a pressure of at least 2.5 bar.

9. The device of claim 1, wherein the guide element is constructed for reversible and non-destructive attachment on, and removal from the hollow body.

10. The device of claim 1, further comprising a handle element arranged on the hollow body.

11. The device of claim 10, wherein the guide element is arranged in a recess formed at a distal end of the handle element.

12. The device of claim 10, wherein the handle element is provided with a groove and wherein the tube line extends in the groove.

13. The device of claim 12, wherein the groove is provided with fixing elements.

14. The device of claim 10, wherein the handle element includes a latching recess, said guide element being fixable in position by reversible, latching engagement in the latching recess through a pivoting motion.

15. The device of claim 14, wherein the latching recess is formed in a border surface of a recessed region of the handle element.

16. The device of claim 14, wherein the guide element is engagable in the latching recess by pivoting about the through hole as rotation axis by 30° to 50°.

17. The device of claim 1, wherein the guide element has a projection which is insertable into the inlet opening in a fluid tight manner up to a projecting stop.

18. The device of claim 17, wherein the projection includes a sleeve which has outer walling in spaced-apart relation from a funnel shaped inner walling of the inlet opening.

19. The device of claim 1, wherein the inlet opening has at least one portion which is configured in the form of a hollow funnel shaped region that conically narrows from a broader starting region.

20. The device of claim 1, further comprising a flange on an outside of the hollow body, said flange being adjustable along the hollow body and detachably fastenable to the hollow body.

21. The device of claim 20, wherein the flange includes a conical sealing portion.

22. The device of claim 1, further comprising an elastic bellow arranged between the guide element and the working tool.

23. The device of claim 1, wherein the working tool comprises a rotating shaft.

24. The device of claim 1 wherein the working tool is constructed as a milling tool, or a rotation free working tool.

25. The device of claim 24, wherein the working tool is constructed as an ultrasound-Osteotome or a laser cutting tool.

26. The device of claim 1, further comprising a manual or automatic pressure control unit, connected with the device via the connection.

27. The device of claim 1, further comprising a device for generating or transmitting mechanical or electromagnetic vibrations to a working medium in the pressure chamber.

28. The device of claim 1, wherein the shaft has a diameter of which decreases stepwise toward a drill head of the working tool, wherein the shaft has a first subsection located in the pressure chamber and a second subsection lying sealingly in a region of the through hole, said first subsection having a diameter which is smaller than a diameter of the second subsection.

29. A set, comprising:
a tube line;
a guide element having a through hole constructed for passage of a shaft of a working tool, said guide element having a connection for connection to the tube line, wherein a channel extends in the guide element separate from the through hole from a first opening formed on the connection to a second opening formed axially offset relative to the through hole on an axial end side of the guide element;
and
a syringe,
wherein the guide element, the tube line and the syringe are sterilized and packaged aseptically in a closed container.

* * * * *